US008933055B2

(12) United States Patent
Pedersen et al.

(10) Patent No.: US 8,933,055 B2
(45) Date of Patent: *Jan. 13, 2015

(54) ANTIMICROBIAL COMPOSITIONS CONTAINING CATIONIC ACTIVE INGREDIENTS AND QUATERNARY SUGAR DERIVED SURFACTANTS

(75) Inventors: Daniel E. Pedersen, Cottage Grove, MN (US); Angela R. Eder, St Paul, MN (US); Charles A. Hodge, Cottage Grove, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/238,860

(22) Filed: Sep. 21, 2011

(65) Prior Publication Data

US 2012/0071438 A1  Mar. 22, 2012

Related U.S. Application Data

(60) Provisional application No. 61/385,341, filed on Sep. 22, 2010.

(51) Int. Cl.
*A01N 43/16* (2006.01)
*A01N 33/12* (2006.01)
*A01N 47/44* (2006.01)
*A01P 1/00* (2006.01)
*A01N 25/16* (2006.01)
*A01N 25/30* (2006.01)

(52) U.S. Cl.
CPC ............... *A01N 25/16* (2013.01); *A01N 25/30* (2013.01)
USPC ............ 514/54; 514/23; 514/53; 514/62; 514/635; 510/123; 510/124; 510/125; 510/126; 510/127; 510/128; 510/129; 510/130; 510/138; 510/204; 510/470

(58) Field of Classification Search
USPC .......... 514/23, 53, 54, 62, 635; 510/123, 124, 510/125, 126, 127, 128, 130, 138, 470, 204
See application file for complete search history.

(56) References Cited

U.S. PATENT DOCUMENTS

| | | | |
|---|---|---|---|
| 4,567,174 A * | 1/1986 | Edwards et al. ......... 514/210.01 |
| 5,188,756 A | 2/1993 | Baker | |
| 5,234,618 A | 8/1993 | Kamegai | |
| 5,376,686 A * | 12/1994 | Ishikawa et al. ............. 514/635 |
| 5,415,814 A | 5/1995 | Ofosu | |
| 5,417,893 A | 5/1995 | Ofosu | |
| 5,653,970 A | 8/1997 | Vermeer | |
| 5,707,959 A | 1/1998 | Pancheri | |
| 5,756,446 A | 5/1998 | Bator | |
| 6,057,274 A | 5/2000 | Bator | |
| 6,221,828 B1 | 4/2001 | Matsuo | |
| 6,323,171 B1 | 11/2001 | Fonsny | |
| 6,384,004 B2 | 5/2002 | McCandlish | |
| 6,387,866 B1 | 5/2002 | Mondin | |
| 6,395,691 B1 | 5/2002 | Tsaur | |
| 6,432,907 B1 | 8/2002 | Skold | |
| 6,730,654 B2 | 5/2004 | Godfroid et al. | |
| 6,764,989 B1 | 7/2004 | Huish | |
| 6,846,492 B2 * | 1/2005 | Haap et al. ..................... 424/405 |
| 6,846,786 B1 | 1/2005 | Patel | |
| 6,881,710 B1 | 4/2005 | O'Lenick, Jr. et al. | |
| 6,906,018 B1 | 6/2005 | Patel | |
| 6,906,023 B1 | 6/2005 | Patel | |
| 6,923,988 B2 * | 8/2005 | Patel et al. ..................... 424/489 |
| 7,084,129 B1 * | 8/2006 | Smith et al. ..................... 514/53 |
| 7,163,914 B2 * | 1/2007 | Gluck et al. ................... 510/131 |
| 7,179,779 B1 | 2/2007 | Hauser | |
| 7,250,392 B1 | 7/2007 | Leonard | |
| 7,345,015 B1 | 3/2008 | Kong et al. | |
| 7,374,779 B2 * | 5/2008 | Chen et al. ..................... 424/451 |
| 7,501,387 B2 | 3/2009 | Aihara | |
| 7,507,399 B1 * | 3/2009 | O'Lenick, Jr. ............. 424/70.11 |
| 7,544,649 B2 | 6/2009 | Aihara | |
| 7,547,672 B2 | 6/2009 | Zaki | |
| 7,897,553 B2 * | 3/2011 | Heiler ........................... 510/112 |
| 2002/0155978 A1 | 10/2002 | Man | |
| 2002/0183233 A1 | 12/2002 | Shuman | |
| 2003/0074742 A1 | 4/2003 | Perry | |
| 2005/0000030 A1 | 1/2005 | Dupont | |
| 2005/0176614 A1 | 8/2005 | Soldanski | |
| 2006/0142174 A1 | 6/2006 | Fukuda | |
| 2008/0161268 A1 | 7/2008 | Yen et al. | |
| 2008/0209645 A1 | 9/2008 | Carrillo | |

(Continued)

FOREIGN PATENT DOCUMENTS

| | | | | | |
|---|---|---|---|---|---|
| EP | 1669061 A1 * | 6/2006 | ............... A61K 8/60 |
| EP | 1669061 B1 | 11/2009 | |
| EP | 1669061 B9 | 3/2010 | |
| WO | WO01/07547 | 2/2001 | |
| WO | WO2006/013315 A1 * | 2/2006 | ............... A61K 8/43 |
| WO | WO2009/029046 | 3/2009 | |

OTHER PUBLICATIONS

M. Claesson; Mikael Kjellin, "Sugar Surfactants", Encyclopedia of Surface and Colloid Science, Royal Institute of Technology, Stockholm, Sweden, Aug. 15, 2006.

(Continued)

*Primary Examiner* — Ganapathy Krishnan
(74) *Attorney, Agent, or Firm* — McKee, Voorhees & Sease

(57) ABSTRACT

The antimicrobial composition of the present invention comprises a cationic active ingredient, a quaternized sugar-derived surfactant, and an optional foam boosting surfactant. These formulations have a high cidal activity in a short amount of time and provide stable copious foam. The formulations of the present invention also exhibit enhanced tissue (e.g. skin) compatibility as defined by an in vitro whole toxicology assessment method.

13 Claims, 8 Drawing Sheets

(56) References Cited

U.S. PATENT DOCUMENTS

2009/0069436 A1    3/2009    MacGregor
2010/0081596 A1    4/2010    Rong

OTHER PUBLICATIONS

Guido Viscardi, Pierluigi Quagliotto, Claudia Barolo, Piero Savarino, Ermanno Barni, and Emilia Fisicaro, "*Synthesis and Surface and Antimicrobial Properties of Novel Cationic Surfactants*", University of Parma, Italy, J. Org. Chem., 2000, 65(24), pp. 8197-8203, Oct. 28, 2000.

Simoes, Manuel, Pereira, Maria Olivia and Maria Joan Vieira "*Action of a cationic surfactant on the activity and removal of bacterial biofilms formed under different flow regimes*", Department of Biological Engineering, University of Minho, Gualtar, Portugal, vol. 39, Issues 2-3, Jan.-Feb. 2005, pp. 478-486.

\* cited by examiner

ANTIMICROBIAL COMPOSITIONS CONTAINING CATIONIC ACTIVE INGREDIENTS AND QUATERNARY SUGAR DERIVED SURFACTANTS

FIELD OF THE INVENTION

The present invention is directed to antimicrobial compositions, like hard surface compositions, having improved antimicrobial effectiveness and high foaming attributes. More particularly, the present invention relates to antimicrobial compositions exhibiting the antimicrobial effectiveness of cationic active ingredients and a polyquaternary functionalized alkyl polyglucoside or a quaternary functionalized alkyl polyglucoside, with optional properties of a high broad spectrum of antimicrobial efficacy, high foam and reduced irritation to mammalian tissue.

BACKGROUND

Antimicrobial personal care compositions are known in the art. Especially useful are antimicrobial cleaning compositions, which typically are used to clean a hard surface and to destroy bacteria and other microorganisms present on the surface.

Antimicrobial compositions are used, for example, in the health care industry; long term care, hospitality and health/exercise facilities; food service industry; meat processing industry; and in the private sector by individual consumers. The widespread use of antimicrobial compositions indicates the importance consumers place on controlling bacteria and other microorganism populations on skin. It is important, however, that antimicrobial populations provide a substantial and broad spectrum reduction in microorganism populations quickly and without problems associated with toxicity and skin irritation.

Several different classes of antimicrobial agents have been used in hard surface antimicrobial compositions. These include active ingredients selected from the following classes: phenolic compounds, carbanalide compounds, lower alcohols, surface active and oxidizing agents; halogens, and the like. Each of these classes has their own unique advantages and challenges. Examples of specific antimicrobial agents include Triclocarban, quaternary ammonium compounds (QAC), iodine and iodine complexes, halogens, phenolic derivatives o-benzylphenol, peroxides and peroxy compounds, and biguanides.

A high foaming disinfectant/antimicrobial composition has specific application for use in the general public and public health areas where it marks where a surface has been treated and can be optionally followed with a water rinse. A high foaming surfactant in a sufficient amount to provide a notable foam profile will often inactivate a quaternary ammonium compound. The present invention provides a unique combination that allows the formulation of high foam systems while not exhibiting detrimental properties to the antimicrobial activity. This has particular utility in such products such as bathroom and shower cleaning and disinfection or wherever a high foam system is preferred.

The antimicrobial compositions are addressed by embodiments of the present invention and will be understood by reading and studying the following specification. The following summary is made by way of example and not by way of limitation. It is merely provided to aid the reader in understanding some of the aspects of the invention.

SUMMARY OF THE INVENTION

The summary of the invention is intended to introduce the reader to various exemplary aspects of the invention. Particular aspects of the invention are shown in other sections herein below, and the invention is set forth in the appended claims which alone demarcate its scope.

In accordance with an exemplary embodiment of the present invention, an antimicrobial composition that exhibits fast efficacy and high foaming attributes is provided. The antimicrobial composition comprises a cationic active ingredient, a quaternized sugar-derived surfactant, a foam boosting surfactant which may encompass nonionic surfactants, amphoteric surfactants, cationic surfactants, anionic surfactants and water or other suitable diluent.

Accordingly, one aspect of the present invention is to provide an antimicrobial hard surface composition, the dilutable concentrate antimicrobial composition comprising: (a) about 0.5 wt. % to about 20 wt. %, by weight of cationic actives; (b) about 0.2 wt. % to about 50 wt. %, by weight, of a quaternized sugar-derived surfactant; (c) about 0.2 wt. % to about 18 wt. %, by weight of an optional foam boosting surfactant; (d) optional adjuvants; and (e) water or other suitable diluent.

Another aspect of the present invention is to provide an antimicrobial hard surface composition, wherein the use solution antimicrobial composition comprising: (a) about 50 ppm to about 5000 ppm by weight of cationic actives; (b) about 50 ppm to about 2500 ppm by weight, of a quaternized sugar-derived surfactant; (c) about 50 ppm to about 10,000 ppm, by weight of an optional foam boosting surfactant; (d) optional adjuvants; and (e) water or other suitable diluent.

Additionally, one aspect of the present invention is to provide a hard surface antimicrobial composition wherein the composition has a relative weight ratio of cationic active to quaternized sugar surfactant to foam boosting surfactant from about 1:0.2:0.2 to about 1:3:8.

Another aspect of the present invention is to provide hard surface sanitizing products based on an antimicrobial composition of the present invention, for example a high foaming hard surface sanitizing cleaner, high foaming hard surface disinfectant cleaner, a tub and tile cleaner and the like.

A further aspect of the present invention is to provide a method of reducing microbial populations including Gram positive and/or Gram negative bacteria, viruses and fungi populations on hard surfaces, by contacting the hard surface, with a composition of the present invention for a sufficient time, such as about 30 seconds to 10 minutes, to reduce the bacteria level to a desired level.

While multiple embodiments are disclosed, still other embodiments of the present invention will become apparent to those skilled in the art from the following detailed description, which shows and describes illustrative embodiments of the invention. Accordingly, the detailed description is to be regarded as illustrative in nature and not restrictive.

The amount and type of cationic active ingredient (0.5% ADBAC Quat) and Quaternary sugar-derived surfactant (1.25% Poly Trimoniumhydroxypropyl Cocoglucosides Chloride) were held constant.

Figure 4:
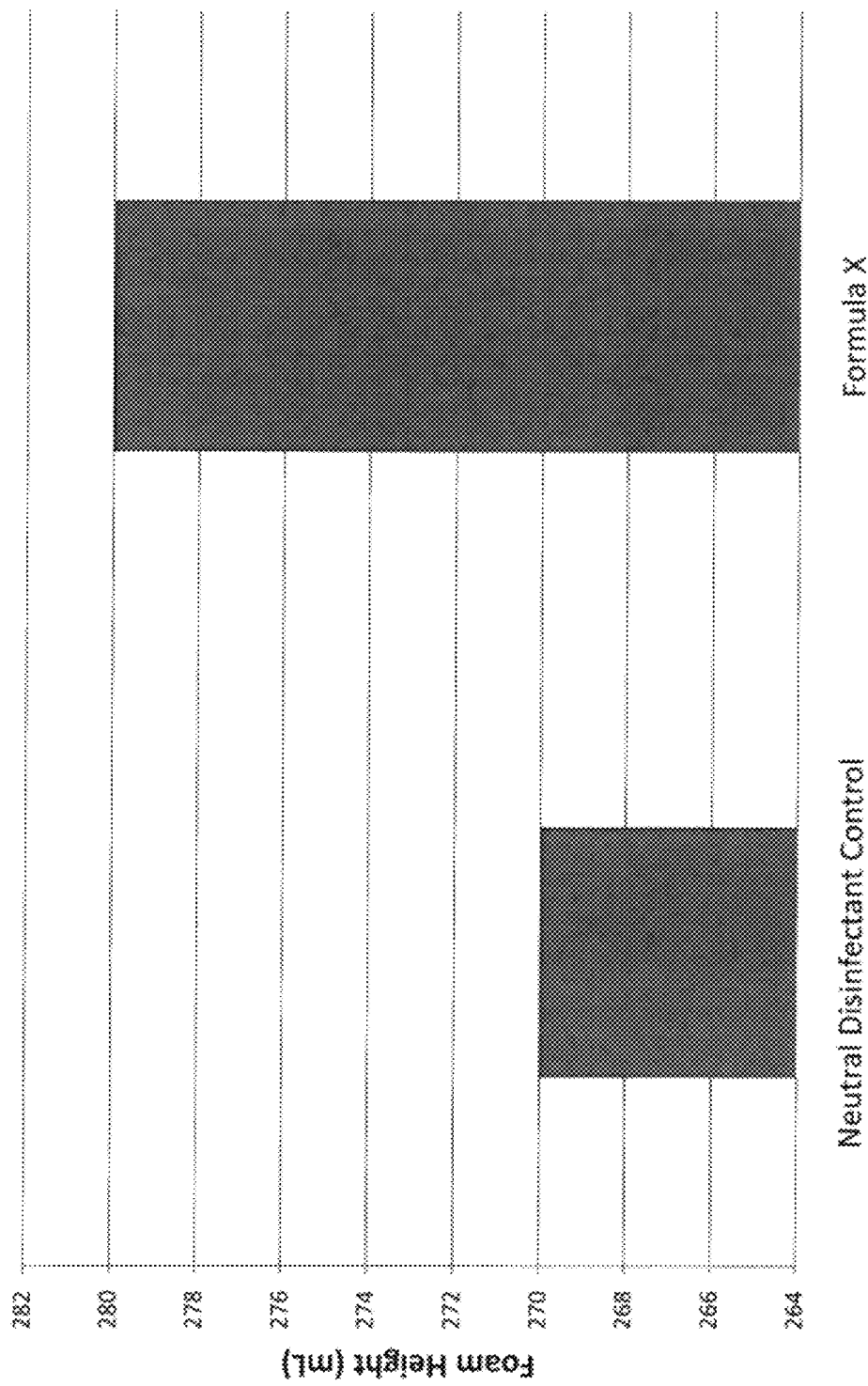

FIG. 4 illustrates the comparative foam volume for a hard surface neutral disinfectant composition of the current invention.

Figure 5:
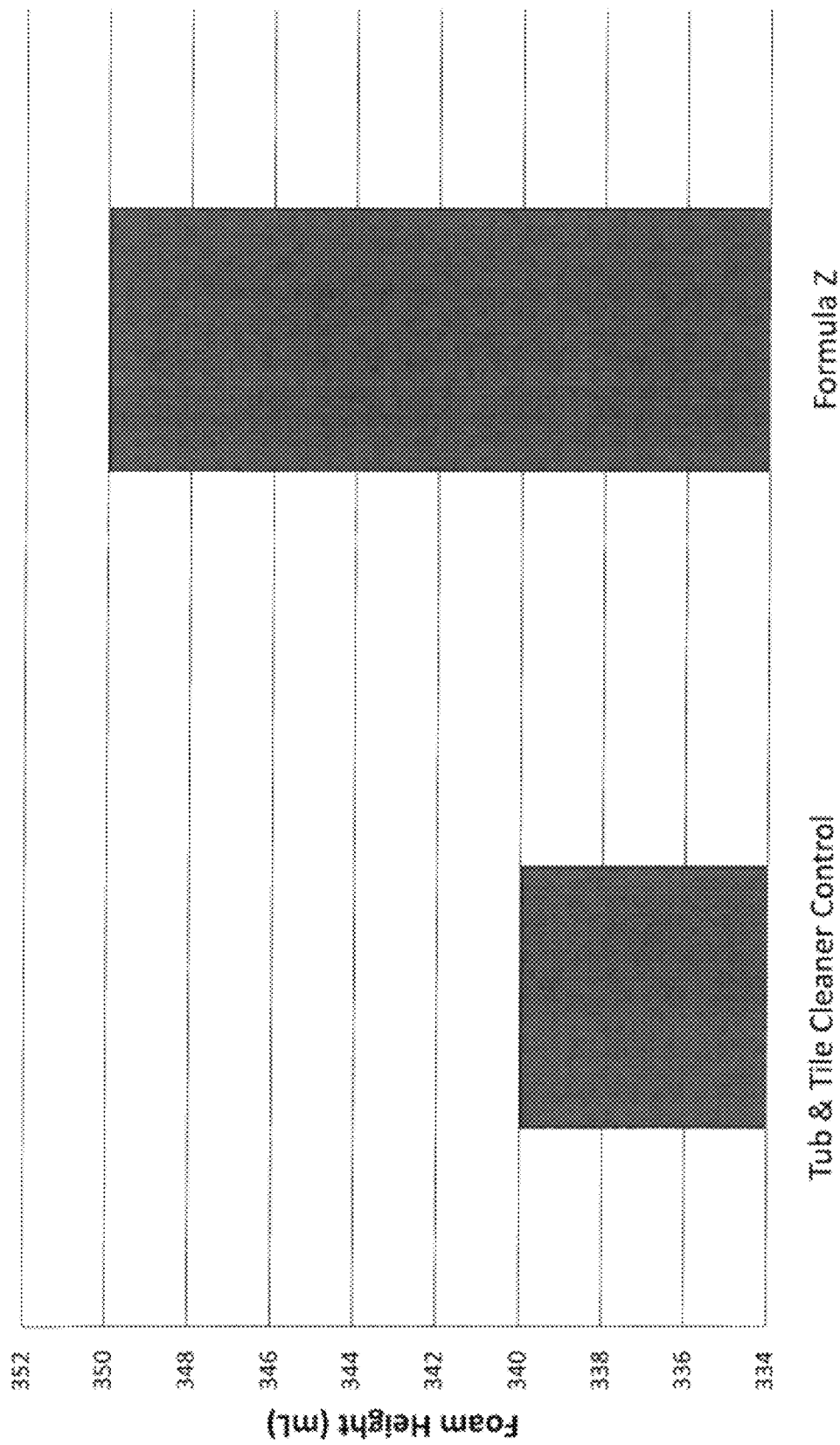

FIG. 5 illustrates the comparative foam volume for a hard surface tub & tile disinfectant composition of the current invention.

Figure 6:
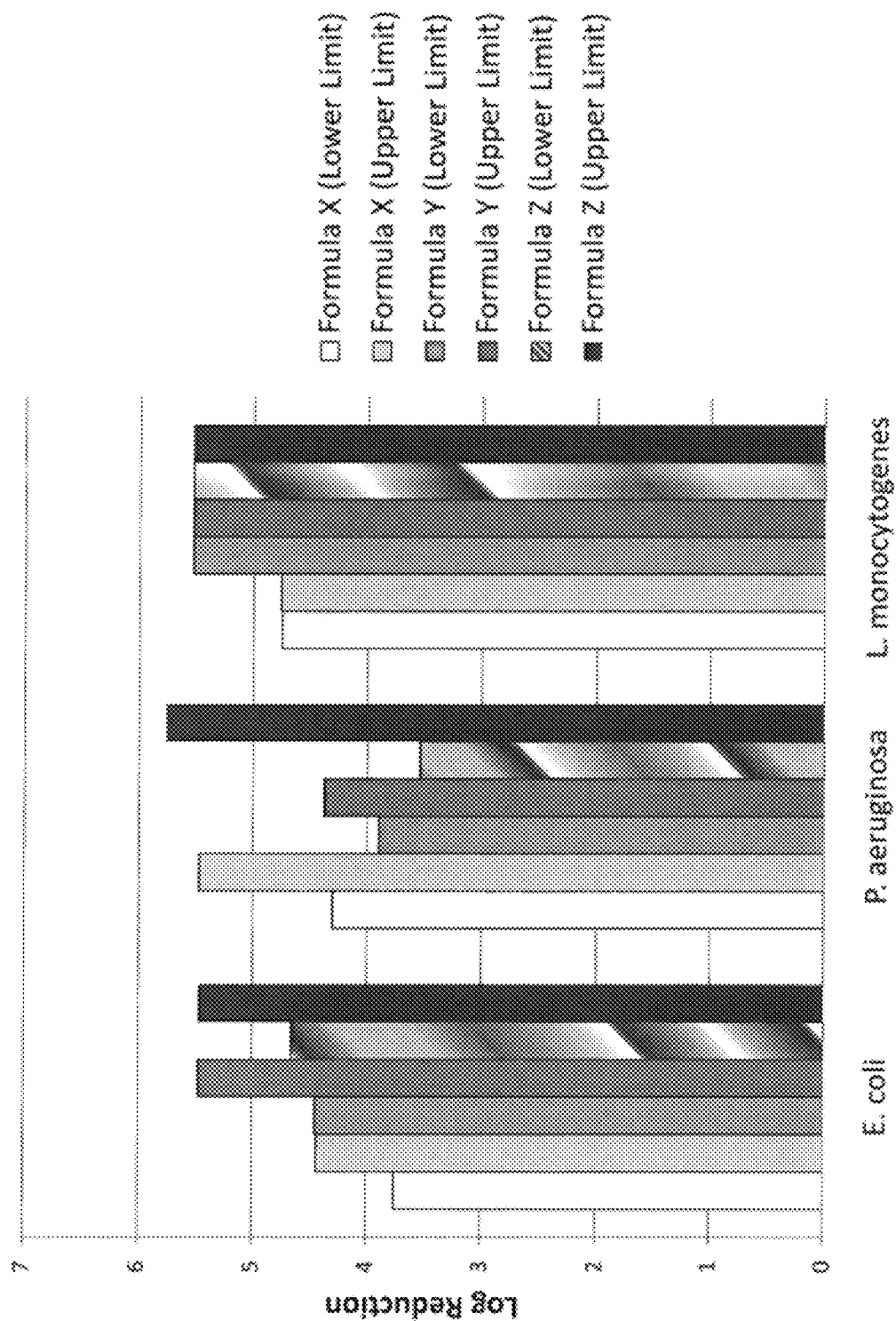

FIG. 6 illustrates the antimicrobial efficacy of hard surface chemistries containing a cationic active and quaternized sugar-derived surfactants of the current invention as disinfectants against key organisms.

Figure 7:
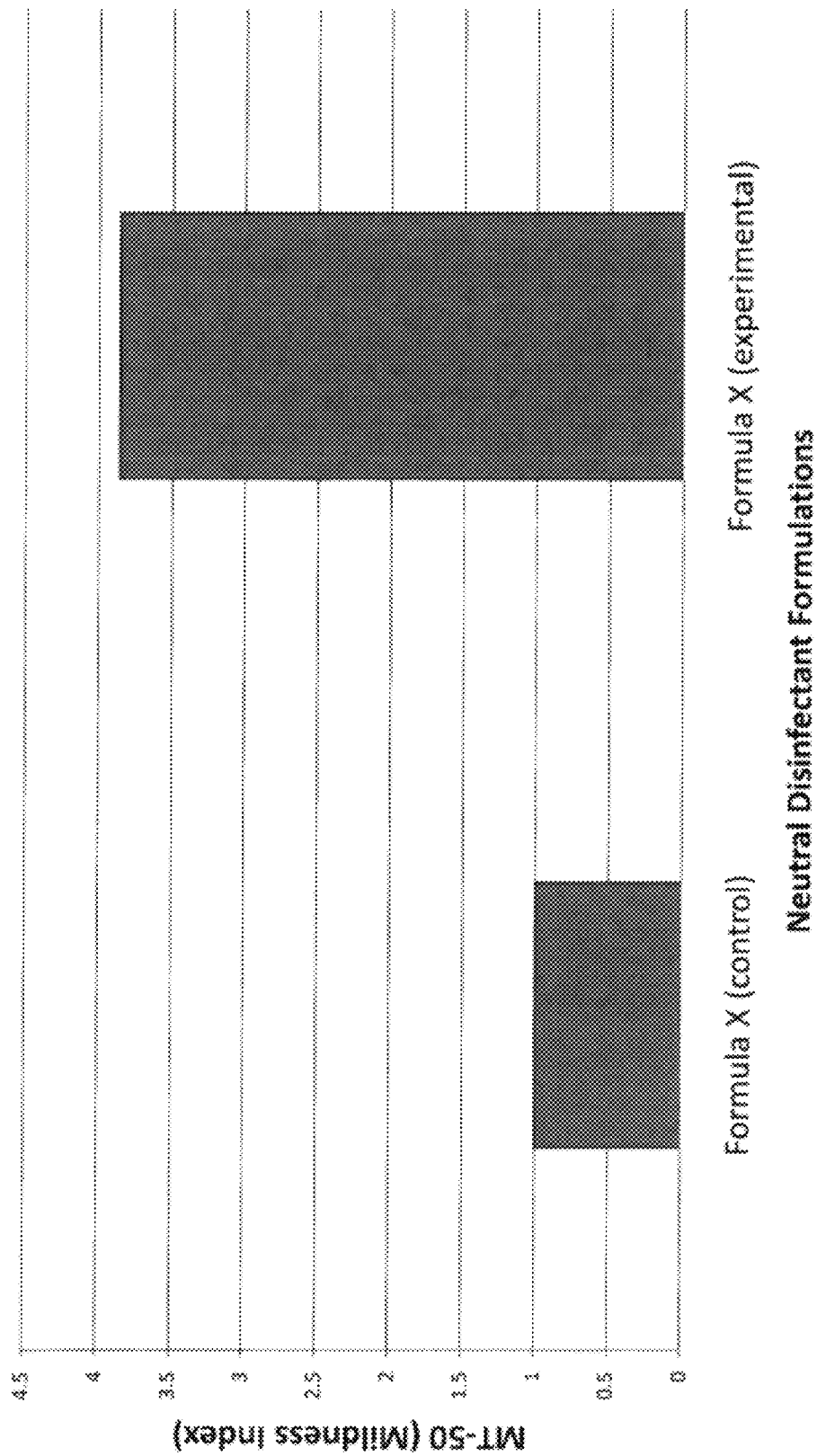

FIG. 7 illustrates the improved skin compatibility of neutral disinfectants when quaternized sugar-derived surfactants are used in combination with cationic active ingredients.

Figure 8:
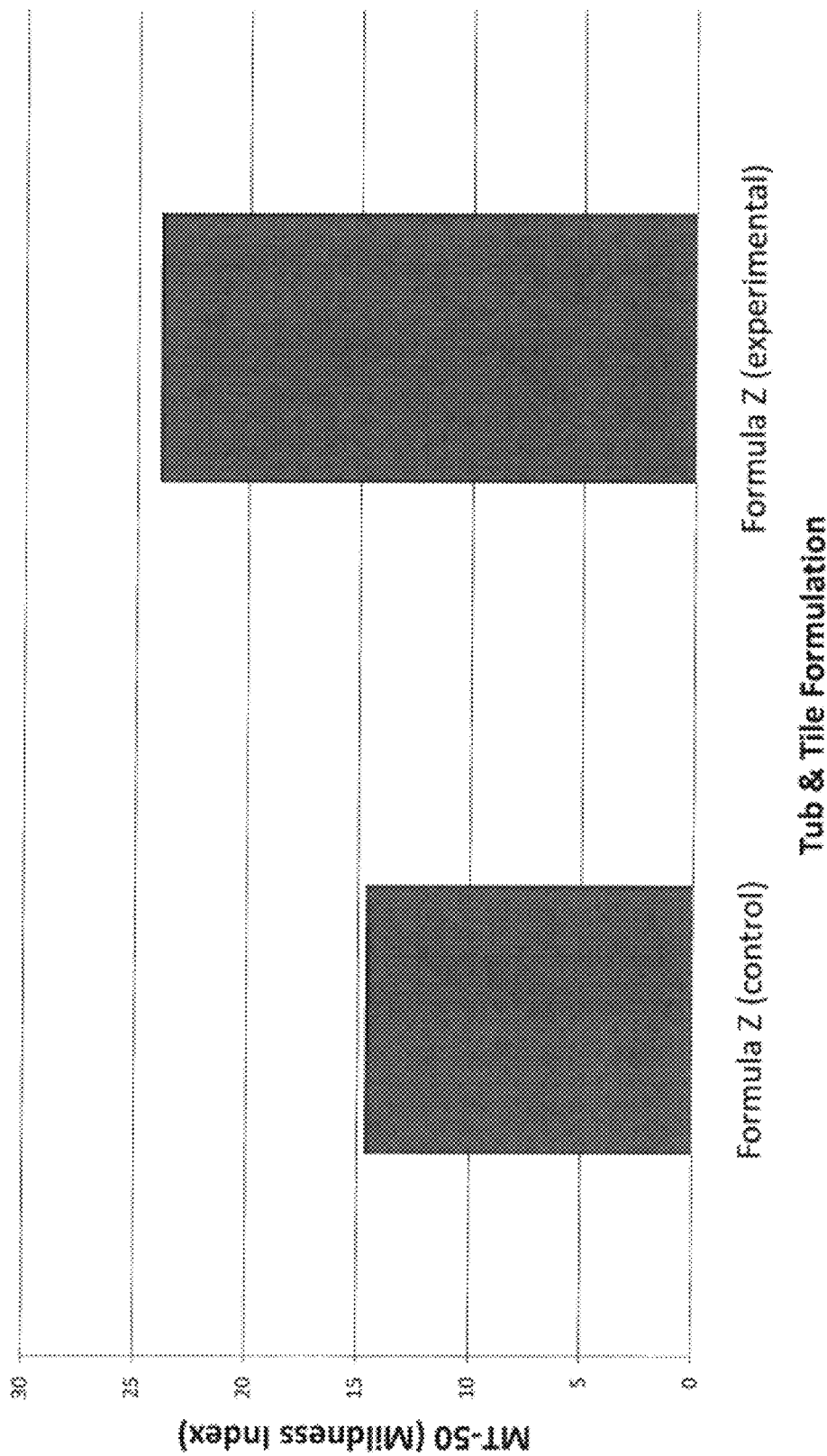

FIG. 8 illustrates the improved skin compatibility of tub & tile disinfectants when quaternized sugar-derived surfactants are used in combination with cationic active ingredients.

DETAILED DESCRIPTION OF THE PREFERRED EMBODIMENTS

Other than in the operating examples, or where otherwise indicated, all numbers expressing quantities of ingredients or reaction conditions used herein are to be understood as being modified in all instances by the term "about".

As used herein, weight percent (wt-%), percent by weight, % by weight, and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

As used herein, the term "cationic active ingredient" refers to a compound that provides antimicrobial cidal activity.

The term "alkyl" refers to a straight or branched chain monovalent hydrocarbon radical having a specified number of carbon atoms. As used herein, "alkyl" refers to a linear or branched substituted or unsubstituted $C_6$-$C_{18}$ carbon chain.

The term "microbial" or "microbial population" refers to bacterial, fungal, yeast, or viral population or combinations thereof, or any mixture thereof in a laboratory or natural setting.

The term "surfactant" or "surface active agent" refers to an organic chemical that changes the properties of that liquid at a surface or interface.

"Cleaning" refers to performing or aiding in soil removal, bleaching, microbial population reduction, rinsing, or combination thereof.

As used herein, the term "substantially free" refers to compositions completely lacking the component or having such a small amount of the component that the component does not affect the effectiveness of the composition. The component may be present as an impurity or as a contaminant and shall be less than 0.5 wt. %. In another embodiment, the amount of the component is less than 0.1 wt. % and in yet another embodiment, the amount of component is less than 0.01 wt. %.

As used herein, the term "hard surface" includes any environmental surface or structural surface including: showers, sinks, toilets, bathtubs, countertops, windows, mirrors, transportation vehicles, floors, and the like. These surfaces can be those typified as "hard surfaces" (such as walls, floors, bedpans etc.)

As used herein, the term "dilutable concentrate" refers to a solution to which water or other suitable diluent may be added; the solution may or may not be substantially free of water or other suitable diluent in the dilutable concentrate form.

As used herein, the term "use solution" refers to a composition with ingredients found at the concentration intended for use. Use solutions may be provided as "ready to use", with no prior dilution needed, or created from a dilutable concentrate.

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleaning expressed as a percentage minus inert ingredients such as water or salts.

Antimicrobial Compositions Containing Cationic Active Compounds and Quaternized Sugar Derived Surfactants The present invention relates to an antimicrobial composition that exhibits fast efficacy and high foaming attributes. The antimicrobial composition comprises a cationic active ingredient, a quaternized sugar-derived surfactant, a foam boosting surfactant which may encompass nonionic surfactants, amphoteric surfactants, selected anionic surfactants, or cationic surfactants and water or other suitable diluent.

In one embodiment, an antimicrobial hard surface dilutable concentrate composition includes: (a) about 0.5 wt. % to about 20 wt. %, by weight of cationic actives; (b) about 0.2 wt. % to about 50 wt. %, by weight, of a quaternized sugar-derived surfactant; (c) about 0.2 wt. % to about 18 wt. %, by weight of an optional foam boosting surfactant; (d) optional adjuvants; and (e) water or other suitable diluent. The relative weight ratio of cationic active ingredient to quaternized sugar surfactant to foam boosting surfactant is from about 1:0.2:0.2 to about 1:3:8.

In a further embodiment, a hard surface antimicrobial use solution composition includes: (a) about 50 ppm to about 5000 ppm by weight of cationic actives; (b) about 50 ppm to about 2500 ppm by weight, of a quaternized sugar-derived surfactant; (c) about 50 ppm to about 10,000 ppm, by weight of an optional foam boosting surfactant; (d) optional adjuvants; and (e) water or other suitable diluent.

Another aspect of the present invention is to provide an antimicrobial hard surface composition which is stable and has a pH of about 7.0 to about 12.0. The present composition may optionally exhibit additional properties, such as copious foam and foam stability and may exhibit reduced tissue irritancy potential.

Another aspect of the present invention is to provide hard surface sanitizing products based on an antimicrobial composition of the present invention, for example a high foaming hard surface sanitizing cleaner, high foaming hard surface disinfectant cleaner, a tub and tile cleaner and the like.

The following illustrates nonlimiting embodiments of the present invention.

A. Cationic Actives

A cationic active is present in an antimicrobial concentrate composition for reducing microbial population on a hard surface of the present invention in an amount of about 0.5% wt. % to about 20 wt. %, and preferably about 2 wt. % to about 18 wt. %, by weight of the composition.

Additionally, a cationic active is present in an antimicrobial use-solution composition for reducing microbial population on a hard surface of the present invention in an amount of about 50 ppm to about 5000 ppm, and preferably about 100 ppm to about 2500 ppm.

The amount of antimicrobial agent in the composition is related to the end use of the composition, the amount of quaternized sugar-derived surfactant and foam boosting surfactant in the composition, and the presence of optional ingredients in the composition. The amount of antimicrobial agent is sufficient to achieve a microbial kill in a short contact time, for example, 15 to 30 seconds.

Cationic active ingredients are an antimicrobial agent useful in the present invention. The cationic or cationically-active ingredients are substances based on nitrogen centered cationic moieties with net positive change. The cationic or cationically-active ingredients are preferably selected from the group consisting of cationic polymers, cationic surfactants, cationic monomers, and betaine with at least one cationic or cationically-active group.

Suitable cationic active ingredients contain quaternary ammonium groups. Suitable cationic active ingredients especially include those of the general formula:

wherein $R^1$, $R^2$, $R^3$ and $R^4$ independently of each other represent alkyl groups, aliphatic groups, aromatic groups, alkoxy groups, alkylamido groups, hydroxyalkyl groups, aryl groups, $H^+$ ions, each with from 1 to 22 carbon atoms, with the provision that at least one of the groups $R^1$, $R^2$, $R^3$ and $R^4$ has at least eight carbon atoms and wherein $X(-)$ represents an anion, for example, a halogen, acetate, phosphate, nitrate or alkyl sulfate, preferably a chloride. The aliphatic groups can also contain cross-linking or other groups, for example additional amino groups, in addition to the carbon and hydrogen atoms.

Cationic active ingredients may include but are not limited to n-alkyl dimethyl benzyl ammonium chloride, alkyl dimethyl ethyl benzyl ammonium chloride, dialkyl dimethyl quaternary ammonium compounds such as didecyl dimethyl ammonium chloride, dioctyl didecyl ammonium chloride, also including quaternary species such as benzethonium chloride and quaternary ammonium compounds with inorganic or organic counter ions such as bromine, carbonate or other moieties including dialkyl dimethyl ammonium carbonates, as well as antimicrobial amines such as N,N-Bis(3-aminopropyl)dodecylamine, other alkyl amines, Chlorhexidine Gluconate, PHMB (Polyhexamethylene biguanide), salt of a biguanide, a substituted biguanide derivative, an organic salt of a quaternary ammonium containing compound or an inorganic salt of a quaternary ammonium containing compound or mixtures thereof.

B. Quaternized Sugar-Derived Surfactant

Additionally, the present antimicrobial hard surface composition contains a quaternized sugar-derived surfactant in an amount of about 0.2% to about 50%, and preferably about 0.5 to about 12%, by weight, of the dilutable concentrate composition.

Moreover, the present antimicrobial hard surface composition contains a quaternized sugar-derived surfactant in an amount of about 50 ppm to about 2500 ppm, and preferably about 50 ppm to about 500 ppm, of the use solution composition.

The amount of quaternized sugar-derived surfactant present in the composition is related to the amount of the cationic active in the composition, to the identity of the quaternized sugar-derived surfactant, and the end use of the composition.

The quaternized sugar-derived surfactant is a quaternized alkyl polyglucoside or a polyquaternized alkyl polyglucoside, and the like.

In one embodiment, the antimicrobial composition of the present invention includes a polyquaternary functionalized alkyl polyglucoside, a cationic active ingredient, water or other suitable diluent, and an optional foam boosting surfactant. The poly quaternary functionalized alkyl polyglucoside is a cationic surfactant naturally derived from alkyl polyglucosides and has a sugar backbone. Poly quaternary alkyl polyglucosides have the following representative formula:

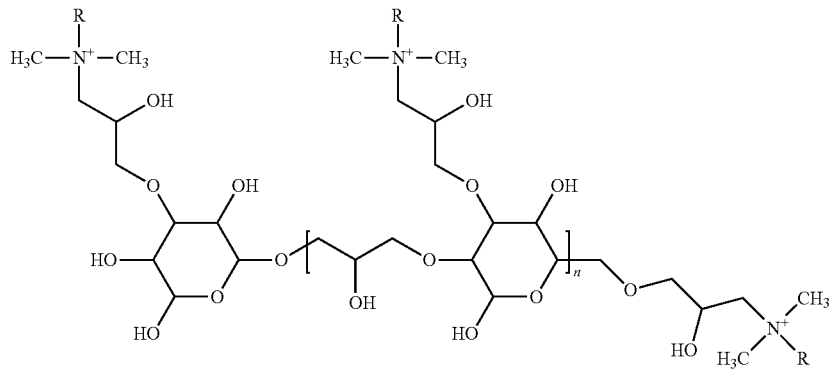

Wherein R is an alkyl group having from about 6 to about 12 carbon atoms and n is an integer ranging from 4 to 6. Examples of suitable poly quaternary functionalized alkyl polyglucosides components which can be used in the cleaning compositions according to the present invention include those in which the R alkyl moiety contains from about 8 to about 12 carbon atoms. In a preferred embodiment the quaternary functionalized alkyl polyglucoside contains primarily about 10-12 carbon atoms. Examples of commercially suitable poly quaternary functionalized alkyl polyglucosides useful in cleaning compositions of the present invention include but is not limited to: Poly Suga® Quat series of quaternary functionalized alkyl polyglucosides, available from Colonial Chemical, Inc., located in South Pittsburg, Tenn.

In another embodiment, the antimicrobial composition of the present invention includes a quaternary functionalized alkyl polyglucoside, a cationic active ingredient, water or other suitable diluent, and an optional foam boosting surfactant. The quaternary functionalized alkyl polyglucoside is a naturally derived cationic surfactant from alkyl polyglucosides and has a sugar backbone. Quaternary functionalized alkyl polyglucosides have the following representative formula:

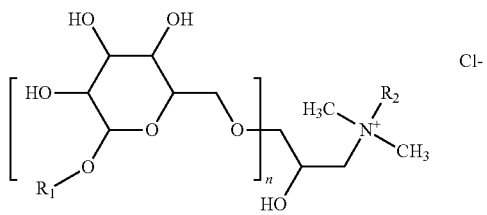

Wherein $R_1$ is an alkyl group having from about 6 to about 22 carbon atoms, and $R_2$ is $CH_3(CH_2)_{n'}$ where n' is an integer ranging from 0-21. Examples of suitable quaternary functionalized alkyl polyglucosides components which can be used in the cleaning compositions according to the present invention include those in which the $R_1$ alkyl moiety contains primarily about 10-12 carbon atoms, the $R_2$ group is $CH_3$ and n is the degree of polymerization of 1-2. Further examples of a suitable quaternary functionalized alkyl polyglucoside include, but are not limited to, the antimicrobial and antifungal quaternary functionalized alkyl polyglucosides described in U.S. Pat. Nos. 7,084,129 and 7,507,399 the disclosures of which are hereby incorporated by reference. Examples of commercially suitable quaternary functionalized alkyl polyglucosides useful in cleaning compositions of the present invention include but is not limited to: Suga® Quat 1212 (primarily $C_{12}$ quaternary functionalized alkyl polyglucoside), Suga®Quat L 1210 (primarily $C_{12}$ quaternary functionalized alkyl polyglucoside), and Suga® Quat S 1218 (primarily $C_{12}$ quaternary functionalized alkyl polyglucoside) available from Colonial Chemical, Inc., located in South Pittsburg, Tenn.

C. Foam-Boosting Co-Surfactant

Additionally, the present antimicrobial hard surface composition may optionally contain a foam boosting surfactant in an amount of about 0% to about 18%, and preferably about 0% to about 9%, by weight, of the composition.

Moreover, the present antimicrobial hard surface composition may optionally contain a foam boosting surfactant in an amount of about 50 ppm to about 3500 ppm, and preferably about 50 ppm to about 500 ppm.

The amount of foam boosting surfactant present in the composition is related to the amount of the cationic active in the composition, the amount of the quaternized sugar-derived surfactant in the composition, the identity of the foam boosting surfactant, and the end use of the composition.

The foam-boosting co-surfactant can be (a) nonionic surfactants, (b) amphoteric surfactants, (c) selected anionic surfactants, (d) cationic surfactants and the like, or (e) mixtures thereof.

Non Ionic Foam Boosting Surfactant

Examples of non ionic foam-boosting co-surfactants include, but are not limited to, alkyl amine oxide, alkyl ether amine oxide, alkyl ether diamines, alkyl alcohol alkoxylates, aryl alcohol alkoxylates, substituted alcohol alkoxylates, block nonionic copolymers, heteric nonionic copolymers, alkanolamides, or polyethoxylated glycerol esters.

The antimicrobial composition can contain a nonionic surfactant component that includes a detersive amount of nonionic surfactant or a mixture of nonionic surfactants. Typically, a nonionic surfactant has a hydrophobic region, such as a long chain alkyl group or an alkylated aryl group, and a hydrophilic group comprising an ethoxy and/or other hydrophilic moieties. As defined herein, a "nonionic foam-boosting co-surfactant" has a hydrophobic region having an alkyl group containing six to eighteen carbon atoms, and an average of one to about twenty ethoxy and/or propoxy moieties. Examples of non ionic foam-boosting co-surfactants include, but are not limited to, alkyl amine oxide, alkyl ether amine oxide, alkyl alcohol alkoxylates, aryl alcohol alkoxylates, substituted alcohol alkoxylates, block nonionic copolymers, heteric nonionic copolymers, alkanolamides, or polyethoxylated glycerol esters, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1-246 and 266-273; in the *CTFA International Cosmetic Ingredient Dictionary, Fourth Ed.*, Cosmetic, Toiletry and Fragrance Association, Washington, D.C. (1991) (hereinafter the *CTFA Dictionary*) at pages 1-651; and in the *CTFA Cosmetic Ingredient Handbook, First Ed.*, Cosmetic, Toiletry and Fragrance Association, Washington, D.C. (1988) (hereafter the *CTFA Handbook*), at pages 86-94, each incorporated herein by reference.

The current invention is substantially free of alkyl phenol ethoxylates. As used herein, the terms "alkyl phenol ethoxylate free" or "NPE-free" refers to a composition, mixture, or ingredients that do not contain alkyl phenol ethoxylates or phenol-containing compounds or to which the same has not been added. Should alkyl phenol etoxylates or alkyl phenol ethoxylate containing compound be present through contamination of a composition, mixture, or ingredients, the amount of the same shall be less than 0.5 wt. %. In another embodiment, the amount of is less than 0.1 wt. % and in yet another embodiment, the amount is less than 0.01 wt. %.

Amphoteric Foam Boosting Surfactant

The antimicrobial composition can contain an amphoteric surfactant component that includes a detersive amount of amphoteric surfactant or a mixture of amphoteric surfactants. Suitable amphoteric surfactants that can be used include, but are not limited to, imidiazolines and imidiazoline derivatives, isethionates, betaine derivatives, amphoacetate derivatives, and mixtures thereof.

Anionic Foam Boosting Surfactant

The antimicrobial composition can contain an anionic surfactant component that includes a detersive amount of an anionic surfactant or a mixture of anionic surfactants. The anionic surfactants that can be used according to the invention include any anionic surfactant available in the cleaning industry. Suitable groups of anionic surfactants include sulfonates and sulfates. Suitable surfactants that can be provided in the anionic surfactant component include, but are not limited to, sarcosine derivatives, succinic acid derivatives, carboxylated alcohols, alkyl sulfate and alkyl ether sulfates, sulfonic acid derivatives, diphenyll sulfonate derivatives, alkyl aryl sulfonic acid derivatives, alkyl polyglucoside sulfonates or sulfates, and mixtures thereof.

Cationic Foam Boosting Surfactant

The antimicrobial composition may contain a cationic surfactant component that includes a detersive amount of cationic surfactant or a mixture of cationic surfactants. Cationic surfactants that can be used in the antimicrobial composition include, but are not limited to, quaternized polysaccharides, alkyl polysaccharides, alkoxylated amines, alkoxylated ether amines, phospholipids, phospholipid derivatives, and mixtures thereof.

D. Carrier

The carrier of the present antimicrobial composition comprises water or other suitable diluent, propylene glycol, glycerols, alcohols or mixtures thereof. It should be appreciated that the water may be provided as deionized water or as softened water. The water provided as part of the concentrate can be relatively free of hardness. It is expected that the water can be deionized to remove a portion of the dissolved solids. That is, the concentrate can be formulated with water that includes dissolved solids, and can be formulated with water that can be characterized as hard water.

The antimicrobial composition of the present invention does not rely upon a low pH or a high pH to provide a rapid reduction in microbial populations. Antimicrobial populations of the present invention have a pH of about 5.0 to about 12.0. Within this pH range, the present compositions effectively reduce microbial populations, and are consumer acceptable, i.e., are mild to the skin, are phase stable, and generate copious, stable foam.

E. Additional Functional Materials

The antimicrobial composition can include additional components or agents, such as additional functional materials. As such, in some embodiments, the antimicrobial composition including the cationic active ingredients and quaternary sugar-derived surfactants may provide a large amount, or even all of the total weight of the antimicrobial composition, for example, in embodiments having few or no additional functional materials disposed therein. The functional materials provide desired properties and functionalities to the antimicrobial composition. For the purpose of this application, the term "functional materials" include a material that when dispersed or dissolved in a use and/or concentrate solution, such as an aqueous solution, provides a beneficial property in a particular use. The antimicrobial composition containing the cationic active ingredients and the quaternized sugar-derived surfactants may optionally contain other disinfectants, sanitizers, dyes, thickening or gelling agents, and perfumes. Some particular examples of functional materials are discussed in more detail below, but it should be understood by those of skill in the art and others that the particular materials discussed are given by way of example only, and that a broad variety of other functional materials may be used. For example, may of the functional material discussed below relate to materials used in disinfecting and/or cleaning applications, but it should be understood that other embodiments may include functional materials for use in other applications.

Dyes and Fragrances

Various dyes, odorants including perfumes, and other aesthetic enhancing agents which are compatible with the invention chemistry may also be included in the antimicrobial composition.

Fragrances or perfumes that may be included in the compositions include, for example, terpenoids such as citronellol, aldehydes such as amyl cinnamaldehyde, a jasmine such as C1S-jasmine or jasmal, vanillin, and the like.

Complexing Agents—Chelators and Sequesterants

In some embodiments, the antimicrobial compositions can optionally include a complexing agent. Complexing agents contribute in water conditioning and divalent ion removal from soils. The complexing agent can include an inorganic complexing agent, an organic complexing agent, and mixtures thereof. Inorganic complexing agents include, but are not limited to, such compounds as sodium pyrophosphate, and sodium tripolyphosphate. Organic complexing agents include, but are not limited to, both polymeric and small molecule complexing agents. Small molecule organic complexing agents include aminocarboxylates such as acids or salts of ethylenediaminetetracetic acid (EDTA) and hydroxy-ethylenediaminetetracetic acid (HEDTA), diethylenetri-aminepentaacetic acid (DTPA), nitrilotriacetic acid (NTA), methylglycinediacetic acid (MGDA), glutamic acid-N,N-diacetic acid, ethylenediaminesuccinic acid (EDDS), 2-hydroxyethyliminodiacetic acid (HEIDA), iminodisuccinic acid (IDS), 3-hydroxy-2,2'-iminodisuccinic acid (HIDS), hydroxymethyliminodiacetate (HIDA), ethylenediaminetet-rapropionates, triethylenetetraminehexacetates, and the respective alkali metal, ammonium and substituted ammonium salts thereof. Phosphonates are also suitable for use as complexing agents in the compositions of the invention and include, but are not limited to ethylenediamine tetra(methyl-enephosphonate), nitrilotrismethylenephosphonate, diethyl-enetriaminepenta(methylene phosphonate), hydroxyeth-ylidene diphosphonate (HEDP), isopropylmethylphosphonic acid (IMPA) and 2-phosphonobutane-1,2,4-tricarboxylic acid (PBTC).

Adjuvants

The present composition can also include any number of adjuvants. In one embodiment adjuvants are present in an amount of about 0% to about 40%, and preferably about 0.2% to about 20%, by weight, of the composition, Specifically, the antimicrobial composition can include solvents and penetrating agents, glycerin, sorbitol, esters, polyquats, glycols, preservatives, chelators, pH additives, pigments or dyes among any number of other constituents which can be added to the composition. Such adjuvants can be pre-formulated with the present composition or added to the system simultaneously, or even after, the addition of the present composition. The antimicrobial composition can also contain any number of other constituents as necessitated by the application, which are known and which can facilitate the activity of the present invention.

Embodiments of the Present Invention

The antimicrobial composition of the present invention has a high broad spectrum of antimicrobial efficacy, high foam and reduced irritation to mammalian tissue. Exemplary compositions are provided in the following tables.

Antimicrobial Hard Surface Cleaners

TABLE 1

| | | Neutral Disinfectant Cleaner Exemplary Composition (Weight Percentage) | | | | | |
|---|---|---|---|---|---|---|---|
| | | Concentrate (Dilutable) | | | | Utility Range | |
| | Neutral Disinfectant | Broadest Range (% w/w) | | Narrowest Range (% w/w) | | (Sanitizing through Disinfecting) (ppm) | |
| | Cleaner (pH 7.2-8.5) | Lower | Upper | Lower | Upper | Lower | Upper |
| Ingredient | Example | Limit | Limit | Limit | Limit | Limit | Limit |
| Cationic Active Ingredient | Didecyl Ammonium Chloride; Alkyl Dimethyl Benzyl Ammonium Chloride | 1.0 | 20.0 | 3.0 | 18.0 | 50.0 | 2000.0 |

TABLE 1-continued

Neutral Disinfectant Cleaner Exemplary Composition (Weight Percentage)

| Neutral Disinfectant Cleaner (pH 7.2-8.5) | | Concentrate (Dilutable) | | | | Utility Range | |
|---|---|---|---|---|---|---|---|
| | | Broadest Range (% w/w) | | Narrowest Range (% w/w) | | (Sanitizing through Disinfecting) (ppm) | |
| Ingredient | Example | Lower Limit | Upper Limit | Lower Limit | Upper Limit | Lower Limit | Upper Limit |
| Quaternized Sugar-Derived Surfactant | Quaternary functionalized alkyl polyglucoside or Polyquaternary functionalized alkyl polyglucoside | 0.2 | 50.0 | 0.9 | 12.0 | 50.0 | 500.0 |
| Foam Boosting Surfactant | Octyl Amine Oxide | 0.0 | 18.0 | 0.0 | 9.0 | 100.0 | 500.0 |
| Adjuvants | Chelators, pH additives, dyes, fragrances | 0.0 | 12.0 | 0.2 | 12.0 | 100.0 | 1000.0 |

TABLE 2

Dilutable Neutral Disinfectant Cleaner Exemplary Composition (Weight Ratio)
Neutral Disinfectant Cleaner (pH 7.2-8.5) (Dilutable)

| Ingredient | Example | Broadest Range (Weight Ratio) | | Narrowest Range (Weight Ratio) | |
|---|---|---|---|---|---|
| | | Lower Limit | Upper Limit | Lower Limit | Upper Limit |
| Cationic Active Ingredient | Didecyl Ammonium Chloride; Alkyl Dimethyl Benzyl Ammonium Chloride | 1.0 | 1.0 | 1.0 | 1.0 |
| Quaternized Sugar-Derived Surfactant | Quaternary functionalized alkyl polyglucoside or Polyquaternary functionalized alkyl polyglucoside | 0.2 | 2.5 | 0.3 | 0.7 |
| Foam Boosting Surfactant | Octyl Amine Oxide | 0.0 | 0.9 | 0.0 | 0.7 |
| Adjuvants | Chelators, pH additives, dyes, fragrances | 0.0 | 0.6 | 0.07 | 0.7 |

TABLE 3

Alkaline Disinfectant Cleaner Exemplary Composition (Weight Percentage)

| Alkaline Disinfectant Cleaner (pH 10.8-11.8) | | Concentrate (Dilutable at 0.5 to 2 oz/gal) | | | | Utility Range | |
|---|---|---|---|---|---|---|---|
| | | Broadest Range (% w/w) | | Narrowest Range (% w/w) | | (Sanitizing through Disinfecting) (ppm) | |
| Ingredient | Example | Lower Limit | Upper Limit | Lower Limit | Upper Limit | Lower Limit | Upper Limit |
| Cationic Active Ingredient | Alkyl Dimethyl Benzyl Ammonium Chloride; Alkyl Dimethyl Ethylbenzyl Ammonium Chloride | 1.0 | 20.0 | 3.0 | 18.0 | 50.0 | 1500.0 |
| Quaternized Sugar-Derived Surfactant | Quaternary functionalized alkyl polyglucoside or Polyquaternary functionalized alkyl polyglucoside | 0.2 | 50.0 | 0.9 | 12.0 | 50.0 | 500.0 |

TABLE 3-continued

Alkaline Disinfectant Cleaner Exemplary Composition (Weight Percentage)

| | | Concentrate (Dilutable at 0.5 to 2 oz/gal) | | | | Utility Range | |
|---|---|---|---|---|---|---|---|
| Alkaline Disinfectant Cleaner (pH 10.8-11.8) | | Broadest Range (% w/w) | | Narrowest Range (% w/w) | | (Sanitizing through Disinfecting) (ppm) | |
| Ingredient | Example | Lower Limit | Upper Limit | Lower Limit | Upper Limit | Lower Limit | Upper Limit |
| Foam Boosting Surfactant | Alcohol Ethoxylate, Amphoteric | 0.0 | 18.0 | 0.0 | 9.0 | 100.0 | 500.0 |
| Adjuvants | Chelators, pH additives, dyes, fragrances | 0.0 | 12.0 | 0.4 | 12.0 | 100.0 | 1000.0 |

TABLE 4

Dilutable Alkaline Disinfectant Cleaner Exemplary Composition (Weight Ratio)
Alkaline Disinfectant Cleaner (pH 10.8-11.8) (Dilutable)

| | | Broadest Range (Weight Ratio) | | Narrowest Range (Weight Ratio) | |
|---|---|---|---|---|---|
| Ingredient | Example | Lower Limit | Upper Limit | Lower Limit | Upper Limit |
| Cationic Active Ingredient | Alkyl Dimethyl Benzyl Ammonium Chloride; Alkyl Dimethyl Ethylbenzyl Ammonium Chloride | 1.0 | 1.0 | 1.0 | 1.0 |
| Quaternized Sugar-Derived Surfactant | Quaternary functionalized alkyl polyglucoside or Polyquaternary functionalized alkyl polyglucoside | 0.2 | 2.5 | 0.3 | 0.7 |
| Foam Boosting Surfactant | Alcohol Ethoxylate, Amphoteric | 0.0 | 0.9 | 0.0 | 0.7 |
| Adjuvants | Chelators, pH additives, dyes, fragrances | 0.0 | 0.6 | 0.1 | 0.7 |

TABLE 5

Tub & Tile Cleaner Exemplary Composition (Weight Percentage)

| | | Concentrate (Dilutable) | | | | Utility Range | |
|---|---|---|---|---|---|---|---|
| Tub & Tile Cleaner (pH 9.5-10.8) | | Broadest Range (% w/w) | | Narrowest Range (% w/w) | | (Sanitizing through Disinfecting) (ppm) | |
| Ingredient | Example | Lower Limit | Upper Limit | Lower Limit | Upper Limit | Lower Limit | Upper Limit |
| Cationic Active Ingredient | Didecyl Ammonium Chlorides & Alkyl Dimethyl Benzyl Ammonium Chloride | 0.5 | 7.0 | 2.0 | 7.0 | 50.0 | 5000.0 |
| Quaternized Sugar-Derived Surfactant | Quaternary functionalized alkyl polyglucoside or Polyquaternary functionalized alkyl polyglucoside | 0.2 | 17.5 | 0.5 | 5.0 | 50.0 | 2500.0 |
| Foam Boosting Surfactant | Alcohol Ethoxylate, Alkyl Polyglucoside, Amine Oxide | 0.0 | 7.0 | 0.0 | 3.5 | 0.0 | 3500.0 |
| Adjuvants | Chelators, pH additives, dyes, fragranes | 0.0 | 40.0 | 0.0 | 20.0 | 50.0 | 10,000.0 |

TABLE 6

Dilutable Tub & Tile Cleaner
Exemplary Composition (Weight Ratio)
Tub & Tile Cleaner (pH 9.5-10.8) (Dilutable)

| Ingredient | Example | Broadest Range (Weight Ratio) | | Narrowest Range (Weight Ratio) | |
|---|---|---|---|---|---|
| | | Lower Limit | Upper Limit | Lower Limit | Upper Limit |
| Cationic Active Ingredient | Didecyl Ammonium Chlorides Alkyl Dimethyl Benzyl Ammonium Chloride | 1.0 | 1.0 | 1.0 | 1.0 |
| Quaternized Sugar-Derived Surfactant | Quaternary functionalized alkyl polyglucoside or Polyquaternary functionalized alkyl polyglucoside | 0.2 | 2.5 | 0.25 | 0.7 |
| Foam Boosting Surfactant | Alcohol Ethoxylate, Alkyl Polyglucoside, Amine Oxide | 0.0 | 1.0 | 0.0 | 0.5 |
| Adjuvants | Chelators, pH additives, dyes, fragrances | 0.0 | 5.7 | 0.0 | 2.8 |

The concentrate composition of the present invention can be provided as a solid, liquid, or gel, or a combination thereof. In one embodiment, the cleaning compositions may be provided as a concentrate such that the cleaning composition is substantially free of any added water or other suitable diluent or the concentrate may contain a nominal amount of water or other suitable diluents. The concentrate can be formulated without any water or other suitable diluent or can be provided with a relatively small amount of water or other suitable diluent in order to reduce the expense of transporting the concentrate. For example, the composition concentrate can be provided as a capsule or pellet of compressed powder, solid, or loose powder, either contained by a water soluble material or not. In the case of providing the capsule or pellet of the composition in a material, the capsule or pellet can be introduced into a volume of water or other suitable diluent, and if present the water soluble material can solubilize, degrade, or disperse to allow contact of the composition concentrate with the water. For the purposes of this disclosure, the terms "capsule" and "pellet" are used for exemplary purposes and are not intended to limit the delivery mode of the invention to a particular shape.

When provided as a liquid concentrate composition, the concentrate can be diluted through dispensing equipment using aspirators, peristaltic pumps, gear pumps, mass flow meters, and the like. This liquid concentrate embodiment can also be delivered in bottles, jars, dosing bottles, bottles with dosing caps, and the like. The liquid concentrate composition can be filled into a multi-chambered cartridge insert that is then placed in a spray bottle or other delivery device filled with a pre-measured amount of water or other suitable diluent.

In yet another embodiment, the concentrate composition can be provided in a solid form that resists crumbling or other degradation until placed into a container. Such container may either be filled with water or other suitable diluent before placing the composition concentrate into the container, or it may be filled with water or other suitable diluent after the composition concentrate is placed into the container. In either case, the solid concentrate composition dissolves, solubilizes, or otherwise disintegrates upon contact with water or other suitable diluent. In a particular embodiment, the solid concentrate composition dissolves rapidly thereby allowing the concentrate composition to become a use composition and further allowing the end user to apply the use composition to a surface in need of cleaning. When the cleaning composition is provided as a solid, the compositions provided herein may be altered in a manner to solidify the cleaning composition by any means known in the art. For example, the amount of water or other suitable diluent may be reduced or additional ingredients may be added to the cleaning composition, such as a solidification agent.

In another embodiment, the solid concentrate composition can be diluted through dispensing equipment whereby water or other suitable diluent is sprayed at the solid block forming the use solution. The diluent flow is delivered at a relatively constant rate using mechanical, electrical, or hydraulic controls and the like. The solid concentrate composition can also be diluted through dispensing equipment whereby diluent flows around the solid block, creating a use solution as the solid concentrate dissolves. The solid concentrate composition can also be diluted through pellet, tablet, powder and paste dispensers, and the like.

It is expected that the concentrate will be diluted with water or other suitable diluent to provide a use solution having a desired level of detersive properties. If the use solution is required to remove tough or heavy soils, it is expected that the concentrate can be diluted with the water of dilution at a weight ratio of at least 1:1 and up to 1:32 or 1:64. If a light duty cleaning use solution is desired, it is expected that the concentrate can be diluted at a weight ratio of concentrate to water of dilution of up to about 1:256.

The concentrate, in liquid form, can contain enough of a compatible diluents to enable the liquid concentrate to be easily converted to a use solution. This may be to overcome dilution variables such as low volume dispensing, or concentrate viscosity as well as dispersion into the diluents and mixing. When the concentrate is provided as a liquid, it may be desirable to provide it in a flowable form so that it can be pumped or aspirated. It has been found that it is generally difficult to accurately pump a small amount of a liquid. It is generally more effective to pump a larger amount of a liquid. Accordingly, although it is desirable to provide the concentrate with as little diluent as possible in order to reduce transportation costs, it is also desirable to provide a concentrate that can be dispensed accurately. In the case of a liquid concentrate, it is expected that diluent will be present in an amount of up to about 90 wt. %, particularly between about 20 wt. % and about 85 wt. %, more particularly between about 30 wt. % and about 80 wt. % and most particularly between about 50 wt. % and about 80 wt. %.

Compositions of the invention may be useful to clean a variety of hard surfaces. Hard surfaces include, but are not limited to, ceramics, ceramic tile, grout, granite, concrete, mirrors, enameled surfaces, metals including aluminum, brass, stainless steel and the like. As such, compositions of the invention are useful to formulate hard surface antimicrobial disinfectants or sanitizers for hard surface sanitization and disinfection use in educational facilities, healthcare facilities, etc., for hard surface disinfection of glazed tile, grout, porcelain, stainless steel, brass, finished wood and painted surfaces, polymeric surfaces, glass and plastic.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Materials used in the described embodiments include, but are not limited to: Stearyldimonium-hydroxypropyl Laurylglucosides Chloride, Cocoglucosides Hydroxypropyl-trimonium Chloride, Laurylglucosides Hydroxypropyl-trimonium Chloride, Poly (Lauryldimonium-hydroxypropyl Decylglucosides Chloride), Poly (Stearyldimonium-hydroxypropyl Decylglucosides Chloride), Poly (Stearyldimonium-hydroxypropyl Laruylglucosides Chloride), Poly (Trimonium-hydroxypropyl Cocoglucosides Chloride).

The following methods were used in the preparation and testing of the examples:

Antimicrobial and Microbial Efficacy:

(1) Determination of Time Kill Activity:
(a) The activity of antimicrobial compositions was measured by the time kill method [ASTM E 2315 *Standard Guide for Assessment of Antimicrobial Activity Using a Time Kill Procedure*], whereby the survival of challenged organisms exposed to an antimicrobial test composition is deterred as a function of time. In this test, a diluted aliquot of the composition is brought into contact with a known population of test bacteria for a specified time period at a specified temperature. The test composition is neutralized at the end of the time period, which arrests the antimicrobial activity of the composition. The percent or, alternatively, log reduction from the original bacteria population is calculated. In general, the time kill method is known to those skilled in the art. In addition, comparative data on the foam profile of representative systems is shown.
(b) The composition can be tested at any concentration from 0.01-100%. The choice of which concentration to use is at the discretion of the investigator, and suitable concentrations are readily determined by those skilled in the art. All testing if performed in triplicate, the results are combined, and the average log reduction is reported.
(c) The choice of contact time period also is at the discretion of the investigator. Any contact time period can be chosen. Typical contact times range from 15 second to 5 minutes, with 30 seconds and 1 minute being typical contact times. The contact temperature also can be any temperature, typically room temperature, or about 25 degrees Celsius.
(d) The microbial suspension, or test inoculum, is prepared by growing a microbial culture on any appropriate solid media (e.g., agar). The microbial population then is washed from the agar with sterile physiological saline and the population of the microbial suspension is adjusted to about $10^8$ colony forming units per ml (cfu/ml).
(e) The table below lists the test microbial cultures used in the following tests and includes the name of the bacteria, the ATCC (American Type Culture Collection) identification number, and the abbreviation for the name of the organism used hereafter.

| Organism Name | ATCC # | Abbreviation |
|---|---|---|
| *Staphylococcus aureus* | 6538 | *S. aureus* |
| *Escherichia coli* | 112229 | *E. coli* |

*S. aureus* is a Gram positive bacteria, whereas, *E. coli* is a Gram negative bacteria.

The log reduction is calculated using the formula:

$$\text{Log reduction} = \log_{10}(\text{numbers control}) - \log_{10}(\text{test sample survivors}).$$

The following table correlates percent reduction in microbial population to log reduction:

| Percent Reduction | Log Reduction |
|---|---|
| 90 | 1 |
| 99 | 2 |
| 99.9 | 3 |
| 99.99 | 4 |
| 99.999 | 5 |

(2) Determination of Disinfection by AOAC Germicidal Spray Test:
(a) The determination of disinfection was evaluated using the AOAC 961.2 *Germicidal Spray Products as Disinfectants* test. A culture of bacteria was dried onto a number of clean, sterile, glass surfaces (e.g. microscope slides). The culture may or may not have been amended with organic soil before application to the test surfaces.
(b) Dry, contaminated, test surfaces were placed in a secondary container (e.g. Petri dish) and sprayed individually with test product. Either 10 or 60 contaminated surfaces may be treated with disinfectant test product.
(c) Contaminated test surfaces were exposed to the disinfectant for a specified contact time.
(d) Following the contact time, the treated test surfaces were individually transferred to sterile test tubes containing growth medium containing an appropriate neutralizer.
(e) The treated test surfaces were incubated 48 hours in the neutralizing medium.
(f) The number of tubes showing growth of the target organism was recorded following incubation compared to those that did not show growth.

Foam Height Determination

The foam height was determined with the following procedural steps:
1. Prepare a 1% solution of the product in 5 grain water.
2. Pour 150 mL of the solution into a blender
3. Mix on medium speed 10 seconds.
4. Pour into a 1000 mL beaker and measure foam height.
5. Measure foam height at 3 and 5 minutes.

Foam Stability Determination

The foam stability was determined by using the difference between the foam/air interference and the foam/aqueous interface 5 minutes after pouring a 1% solution into a 1000 mL beaker.

In Vitro Irritancy Determination

In vitro irritancy was assessed by an external testing facility using Matek Corporation's "EpiDerm MTT ET-50 Protocol (EPI-200)".

The test consists of a topical exposure of the neat test chemical to a reconstructed human epidermis (RhE) model followed by a cell viability test. Cell viability is measured by dehydrogenase conversion of MTT [(3-4,5-dimethyl thiazole 2-yl) 2,5-diphenyltetrazolium bromide], present in cell mitochondria, into a blue formazan salt that is quantitatively measured after extraction from tissues. The reduction of the viability of tissues exposed to chemicals in comparison to negative controls (treated with water) is used to predict the skin irritation potential.

EpiDerm tissues are conditioned by incubation of release transport-stress related compounds and debris overnight.

After pre-incubation, tissues are topically exposed to the test chemicals for 60 minutes. Preferably, three tissues are used per test chemical (TC) and for the positive control (PC) and negative control (NC). Tissues are then thoroughly rinsed, blotted to remove the test substances, and transferred to fresh medium. Tissues are incubated for 42 hrs. Afterwards, the MTT assay is performed by transferring the tissues to 24-well plates containing MTT medium (1 mg/mL). after a 3 hr MTT incubation, the blue formazan salt formed by cellular mitochondria is extracted with 2.0 mL/tissue of isopropanol and the optical density of the extracted formazan is determined using a spectrophotometer at 570 nm. Relative cell viability is calculated for each tissue as % of the mean of the negative control tissues. Skin irritation potential of the test material is predicted if the remaining relative cell viability is below 50%.

The following Figures demonstrate efficacy data of the present antimicrobial composition, using various cationic active ingredients, quaternary sugar-derived surfactants and optional foam boosting surfactants.

Figure 1:
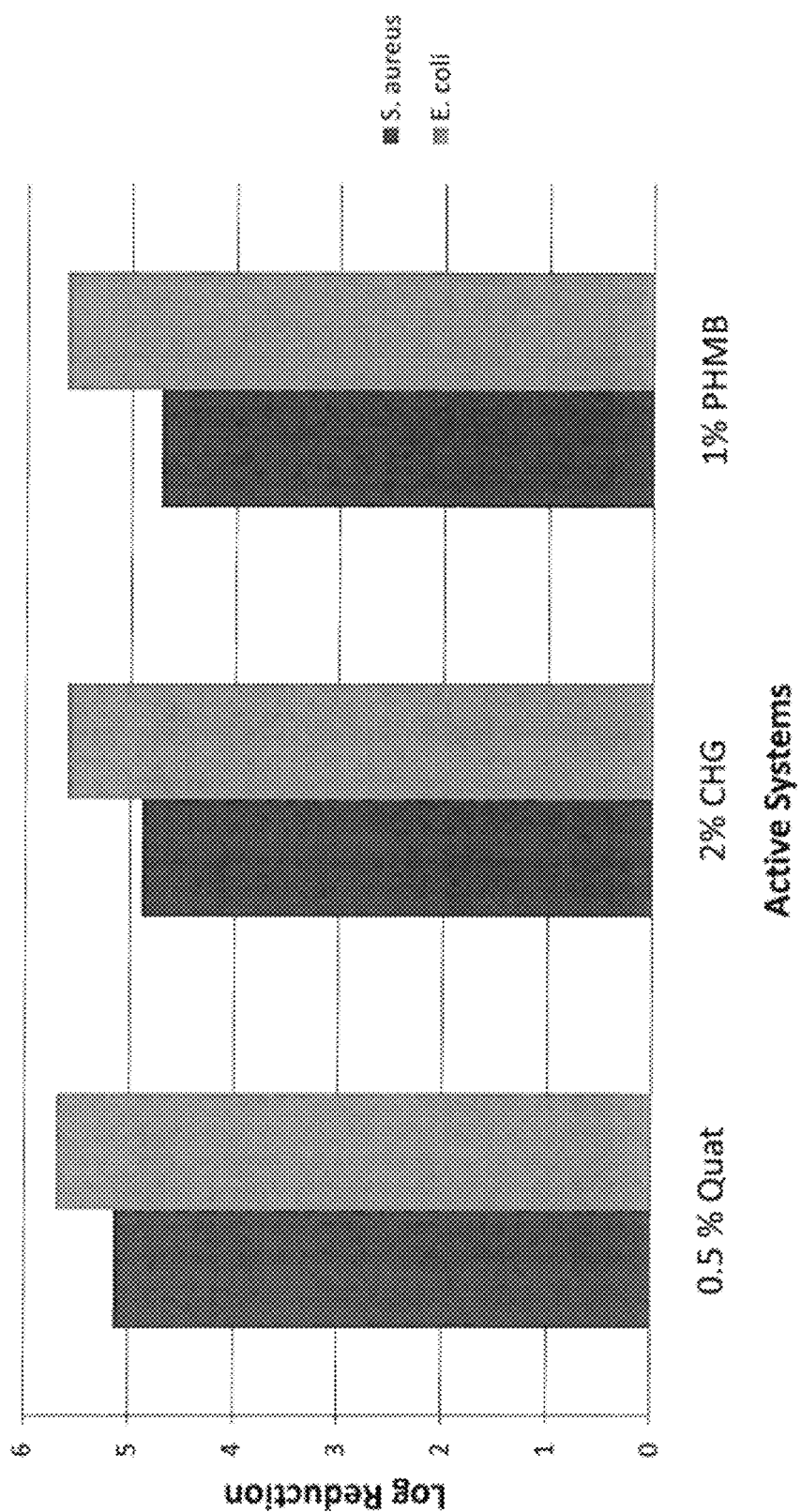
FIG. 1 illustrates the efficacy following a 30 second exposure time of three different cationic active ingredients, specifically, 0.5% Quat (Benzalkonium Chloride), 2% CHG (Chlorhexidine Gluconate), and 1% PHMB (polyhexamethylene biguanide) in a representative surfactant system.

Table 7 and FIG. 1 (Log Reduction of Cationic Active Ingredients): Table 7 and FIG. 1 illustrate the efficacy following a 30 second exposure time of three different cationic active ingredients, specifically, 0.5% Quat (Benzalkonium Chloride), 2% CHG (Chlorhexidine Gluconate), and 1% PHMB (polyhexamethylene biguanide) in a representative surfactant system.

Table 7 illustrates the formulas for the three cationic active ingredient systems tested. Both the quaternary sugar-derived surfactant and foam boosting surfactant were held constant and only the cationic active ingredient was changed between the three tests performed. The results are illustrated in FIG. 1.

TABLE 7

| Active Ingredient System | Ingredients | Level (% w/w) |
| --- | --- | --- |
| Quaternary Ammonium Compound (Quat) | Active Ingredient | 0.5 |
| | Quaternized Sugar-Derived Surfactant | 1.25 |
| | Foam Boosting Agent | 1.95 |
| Chlorhexidine Gluconate (CHG) | Active Ingredient | 2.0 |
| | Quaternized Sugar-Derived Surfactant | 1.25 |
| | Foam Boosting Agent | 1.95 |
| Poly Hexamethylene Biguanide (PHMB) | Active Ingredient | 1.0 |
| | Quaternized Sugar-Derived Surfactant | 1.25 |
| | Foam Boosting Agent | 1.95 |

As illustrated in FIG. 1, all three cationic active ingredients had high cidal activity against *S. aureus* and *E. coli* bacteria within a 30 second exposure time.

Figure 2:
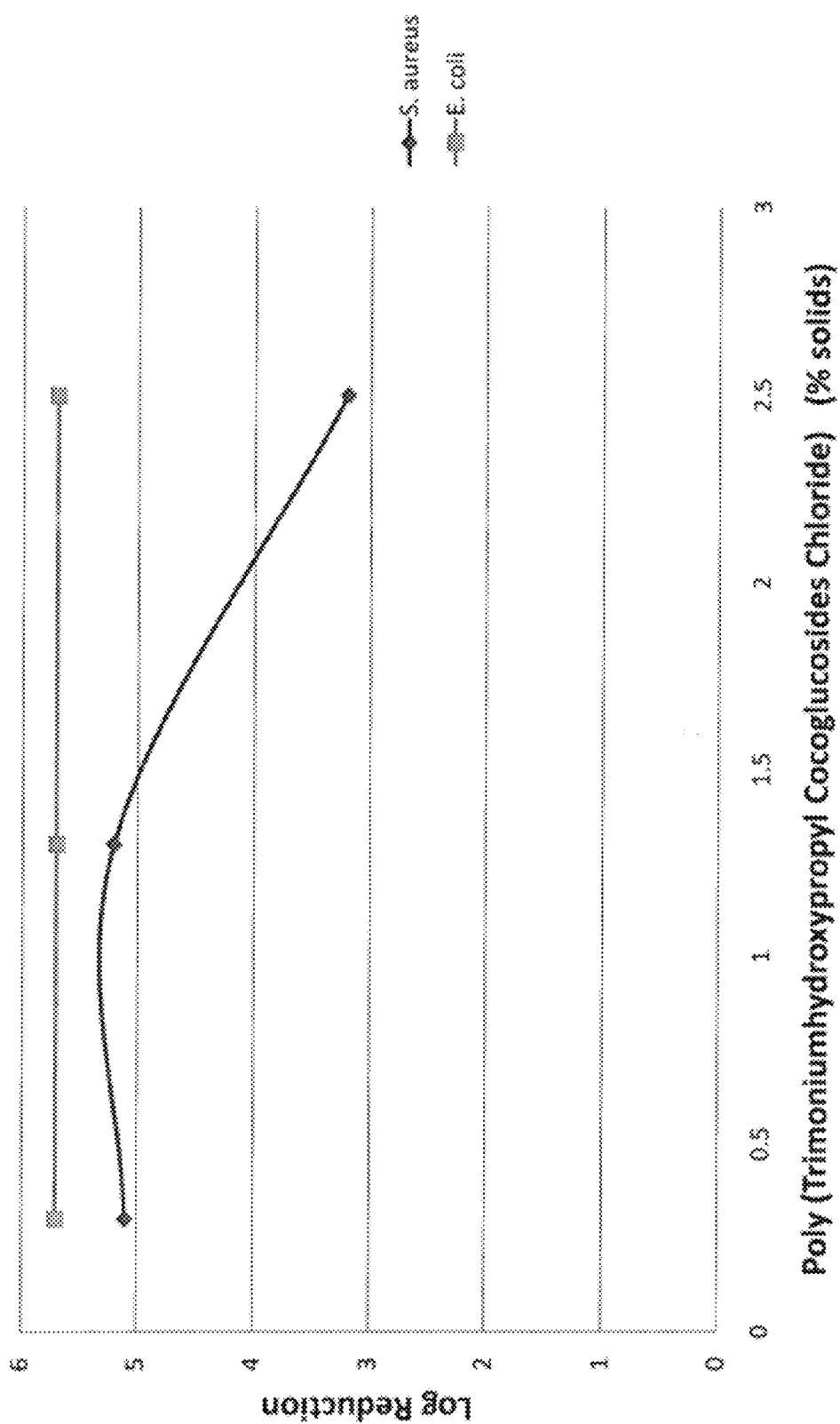
FIG. 2 illustrates the efficacy against *S. aureus* and *E. coli* bacteria with increased concentrations of quaternary sugar-derived surfactants, specifically, Poly (Trimoniumhydroxypropyl Cocogluocosides Chloride). The amount and type of cationic active ingredient (0.5% ADBAC Quat) and foam boosting surfactant (1.95% Alkyl Dimethyl Amine Oxide) was held constant.

Table 8 and FIG. 2 (Log Reduction of Quaternary Sugar-Derived Surfactants): Next, Applicants tested the efficacy at 30 second exposure against *S. aureus* and *E. coli* bacteria with increased concentrations of quaternary sugar-derived surfactants, specifically, Poly (Trimoniumhydroxypropyl Cocogluocosides Chloride). The amount and type of cationic active ingredient (0.5% ADBAC Quat) and foam boosting surfactant (1.95% Alkyl Dimethyl Amine Oxide) was held constant. Table 8 below illustrates the quantitative results of this test and FIG. 2 illustrates the graphical results.

TABLE 8

| Quaternized Sugar-Derived Surfactant (% w/w) | Active Ingredient (% w/w) | Foam Boosting Agent (% w/w) | *S. aureus* Log Reduction | *E. coli* Log Reduction |
| --- | --- | --- | --- | --- |
| 0.3 | 0.5 | 1.95 | >5.0 | >5.0 |
| 1.3 | 0.5 | 1.95 | >5.0 | >5.0 |
| 2.5 | 0.5 | 1.95 | 3.2 | >5.0 |

As Table 8 and FIG. 2 illustrate, the quaternary sugar-derived surfactant has a high cidal activity against *S. aureus* and *E. coli* bacteria after only 30 seconds of exposure. Also, the tolerance of the quaternary sugar derived surfactant against bacteria is shown. Furthermore, it is clearly illustrated that an increased concentration of quaternary sugar-derived surfactant maintains a significant and unexpectedly high log reduction of bacteria up until a 1 to 4 ratio of quaternary sugar-derived surfactant to cationic active ingredients.

Figure 3:
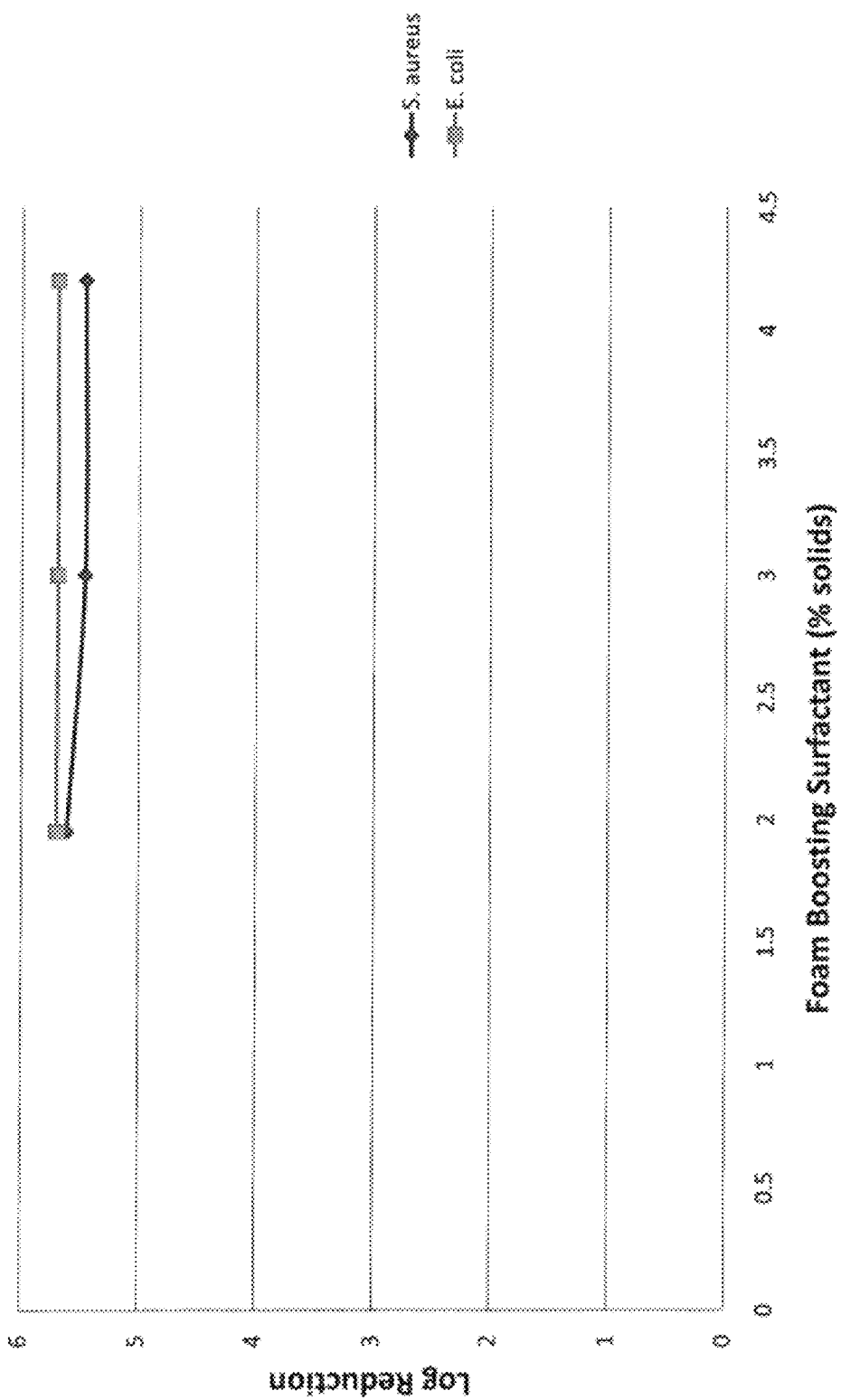
FIG. 3 illustrates the efficacy with increased concentrations of foam boosting surfactants, specifically, amine oxide.

Table 9 and FIG. 3 (Log Reduction of Foam Boosting Surfactants): Table 9 and FIG. 3 illustrate the efficacy with increased concentrations of foam boosting surfactants, specifically, amine oxide. The amount and type of cationic active ingredient (0.5% ADBAC Quat) and Quaternary sugar-derived surfactant (1.25% Poly Trimoniumhydroxypropyl Cocoglucosides Chloride) were held constant. Table 9 below illustrates the quantitative results of this test and FIG. 3 illustrates the graphical results.

TABLE 9

| Foam Boosting Agent (% w/w) | Active Ingredient (% w/w) | Quaternized Sugar-Derived Surfactant (% w/w) | *S. aureus* Log Reduction | *E. coli* Log Reduction |
| --- | --- | --- | --- | --- |
| 1.95 | 0.5 | 1.25 | >5.5 | >5.5 |
| 3.0 | 0.5 | 1.25 | >5.5 | >5.5 |
| 4.2 | 0.5 | 1.25 | >5.5 | >5.5 |

As Table 9 and FIG. 3 illustrate, the foam boosting surfactant has a high cidal activity against *S. aureus* and *E. coli* bacteria after only 30 seconds of exposure. Also, the tolerance of the foam boosting surfactant against bacteria is shown. Furthermore, it is clearly illustrated that a broad range of foam boosting surfactant maintains a significant log reduction of bacteria.

Table 10 (Efficacy of Cationic Actives in Combination with Quaternary Sugar Derived Surfactants and Alkyl Dimethyl Amine Oxide): Applicants tested the efficacy against *S. aureus* and *E. coli* bacteria with various quaternary sugar-derived surfactants, held constant at 1.25%. The amount and type of cationic active ingredient (0.5% ADBAC Quat) and foam boosting surfactant (1.95% Alkyl Dimethyl Amine Oxide) was held constant.

TABLE 10

| Quaternized Sugar-Derived Surfactant (1.25% w/w) | Active Ingredient (% w/w) | Foam Boosting Surfactant (% w/w) | *S. aureus* Log Reduction | *E. coli* Log Reduction |
| --- | --- | --- | --- | --- |
| (L8610) Lauridimonium-hydroxypropyl Cocoglucosides Chloride | 0.5 | 1.95 | >5.0 | >5.0 |
| (L1210) Lauridimonium-hydroxypropyl Laurylglucosides Chloride | 0.5 | 1.95 | >5.0 | >5.0 |

TABLE 10-continued

| Quaternized Sugar-Derived Surfactant (1.25% w/w) | Active Ingredient (% w/w) | Foam Boosting Surfactant (% w/w) | S. aureus Log Reduction | E. coli Log Reduction |
|---|---|---|---|---|
| (S1218) Stearyldimonium-hydroxypropyl Laurylglucosides Chloride | 0.5 | 1.95 | >5.0 | >5.0 |
| (TM8610) Cocoglucosides Hydroxypropyl-trimonium Chloride | 0.5 | 1.95 | >5.0 | >5.0 |
| (TM1212) Laurylglucosides Hydroxypropyl-trimonium Chloride | 0.5 | 1.95 | >5.0 | >5.0 |
| (L1010P) Poly (Lauryldimonium-hydroxypropyl Decylglucosides Chloride) | 0.5 | 1.95 | >5.0 | >5.0 |
| (S1010P) Poly (Stearyldimonium-hydroxypropyl Decylglucosides Chloride) | 0.5 | 1.95 | >5.0 | >5.0 |
| (S1210P) Poly (Stearyldimonium-hydroxypropyl Laruylglucosides Chloride) | 0.5 | 1.95 | >5.0 | >5.0 |
| (TM8610P) Poly (Trimonium-hydroxypropyl Cocoglucosides Chloride) | 0.5 | 1.95 | >5.0 | >5.0 |

As Table 10 illustrates, a significant log reduction is maintained against *S. aureus* and *E. coli* bacteria for both quaternized sugar-derived surfactants and polyquaternized sugar-derived surfactants. The chain length of the sugar quaternary surfactant may be altered and yet still maintain high efficacy.

Tables 11, 12 and 13 (Formulas Used for Hard Surface Testing): Tables 11-13 below illustrate the test formulas used for the tests performed for comparative foam volume and antimicrobial efficacy.

TABLE 11

Neutral Disinfectant Cleaner Concentrate (pH: 7.2-8.5)

| Component | Control (wt %) | Formula X (wt %) |
|---|---|---|
| Water | 83.04 | 83.04 |
| Adjuvants (chelators, pH additive) | 3.3 | 3.3 |
| Cationic Active | 10.16 | 10.6 |
| Foam Boosting Surfactant | 3.5 | |
| Quaternized Sugar-Derived Surfactant | | 3.5 |

TABLE 12

Alkaline Disinfectant Cleaner Concentrate (pH: 10.8-11.8)

| Component | Control (wt %) | Formula Y (wt %) |
|---|---|---|
| Water | 84.7 | 80.8 |
| Adjuvants (chelators, pH additive) | 5.2 | 5.2 |
| Cationic Active | 6.2 | 6.2 |
| Foam Boosting Surfactant | 3.9 | |
| Quaternized Sugar-Derived Surfactant | | 7.8 |

TABLE 13

Tub & Tile Disinfectant Cleaner Concentrate (pH: 9.5-10.8)

| Component | Control (wt %) | Formula Z (wt %) |
|---|---|---|
| Water | 56.2 | 54.5 |
| Adjuvants (chelators, pH additive) | 35 | 35 |
| Foam Boosting Surfactant | 2.8 | |
| Cationic Active 1 | 1 | 1 |
| Cationic Active 2 | 5 | 5 |
| Quaternized Sugar-Derived Surfactant | | 4.5 |

FIGS. 4 and 5 (Comparative Foam Volume for Hard Surface Applications): Foam volumes were tested for the neutral disinfectant cleaner and the tub & the cleaner. As can be seen in FIGS. 4 and 5, the addition of a quaternized sugar derived surfactant in replacement of a foam boosting surfactant actually created greater foam volume. Clearly, the formulas of the current invention generate more copious foam than existing chemistries.

Tables 14 and 15 (Log Reduction of Key Organisms): *E. coli* and *L. monocytogenese* are two important environmental pathogens. Both are known to cause acute enteric infections with broad medical implications. Both organisms are environmental contaminants and can be transferred to food stuffs during manufacture. Data included in Tables 14 and 15 exemplify the utility of the compositions containing a cationic active and quaternized sugar-derived surfactants in controlling these environmental organisms with even a short exposure time.

Table 14 corresponds to FIG. 6 and shows the log reduction of key organisms in the utility range of use solutions for hard surface disinfection (30 sec exposure).

TABLE 14

| Antimicrobial Composition | Formula (ppm Quat) | Log Reduction in 30 sec | | |
|---|---|---|---|---|
| | | E. coli | P. aeruginosa | L. monocytogenes |
| Neutral Disinfectant | 50 | 4.0 | 3.1 | 5.4 |
| | 100 | 5.5 | 3.1 | 5.4 |
| | 200 | 5.5 | 4.0 | 4.6 |
| | 400 | 5.5 | 4.4 | 5.4 |
| | 1500 | 5.5 | 4.8 | 5.5 |
| Alkaline Disinfectant | 50 | 5.3 | 3.7 | 4.8 |
| | 100 | 4.2 | 3.7 | 5.2 |
| | 200 | 5.5 | 3.8 | 5.4 |
| | 400 | 5.5 | 4.2 | 5.4 |
| | 1500 | 5.5 | 4.4 | 5.5 |
| Tub & Tile Disinfectant | 50 | 4.2 | 3.8 | 4.2 |
| | 100 | 5.5 | 3.0 | 5.4 |
| | 200 | 5.5 | 4.3 | 5.4 |
| | 400 | 5.5 | 4.0 | 5.4 |
| | 500 | 5.5 | 5.8 | 5.5 |

Table 15 shows the efficacy of key formulations at 10 minutes exposure for *E. coli* and *L. monocytogenes* as tested via the Germicidal Spray test described above. Formulations were tested at the limits of the utility range for a use solution.

TABLE 15

| Antimicrobial Composition | Formula (Active Limit) | # Negative Tubes/# Carriers Tested | |
|---|---|---|---|
| | | P. aeruginosa | L. monocytogenes |
| Neutral Disinfectant | Lower | 9/10 | 9/10 |
| | Upper | 10/10 | 10/10 |
| Alkaline Disinfectant | Lower | 10/10 | 9/10 |
| | Upper | 10/10 | 10/10 |
| Tub & Tile Disinfectant | Lower | 10/10 | 9/10 |
| | Upper | 10/10 | 10/10 |

FIG. 6 (Antimicrobial Efficacy for Hard Surface Applications): The efficacy of hard surface chemistries containing a cationic active and quaternized sugar derived surfactants were tested against key organisms. As FIG. 6 clearly shows the hard surface chemistries disclosed in the current invention as efficacious against key organisms in as little exposure time as 30 seconds.

Table 16 and FIGS. 7 and 8: Antimicrobial compositions which exhibit reduced tissue irritancy potential are of particular utility in the marketplace. Dermal compatible, efficacious products increase use-frequency thereby promoting good hygiene and decrease negative worker impact. Additionally, enhanced skin compatibility leads to greater worker safety and better worker health through skin integrity and improved procedural cleaning guideline compliance in manual sanitization figures. Table 16 listed below clearly documents the increase in skin compatibility within the field of the invention indicated by the increase in the MT-50 value, or Mildness Index of the experimental formulas in comparison to the controls.

TABLE 16

| Exemplary Formula | MT-50 ("Mildness Index") |
|---|---|
| Formula X (control Neutral Disinfectant) | 1.0 |
| Formula X (experimental Neutral Disinfectant) | 3.9 |
| Formula Z (control Tub & Tile Disinfectant) | 14.7 |
| Formula Z (experimental Tub & Tile Disinfectant | >24 |

These results clearly show the impact of the interaction of his novel approach in reducing the skin irritation and/or increasing the skin compatibility of these disinfectant formulas by a wide margin, moving the chemistries from an irritating to a non-irritating category. FIG. 7 illustrates the improved skin compatibility of Neutral Disinfectants when quaternized sugar-derived surfactants are used in combination with cationic active ingredients. FIG. 8 illustrates the improved skin compatibility of Tub & Tile Disinfectants when quaternized sugar-derived surfactants are used in combination with cationic active ingredients.

Obviously, many modifications and variations of the invention as hereinbefore set forth can be made without departing from the spirit and scope thereof, and, therefore, only such limitations should be imposed as are indicated by the appended claims.

We claim:

1. An antimicrobial hard surface cleaner composition comprising:
   (a) about 0.5 wt. % to about 20 wt. % of a cationic active ingredient selected from the group consisting of a salt of a biguanide, a biguanide derivative, an organic salt of a quaternary ammonium containing compound or an inorganic salt of a quaternary ammonium containing compound;
   (b) about 0.2 wt. % to about 50 wt. % of a quaternized sugar-derived surfactant that is a polyquaternized alkyl polyglucoside of the formula

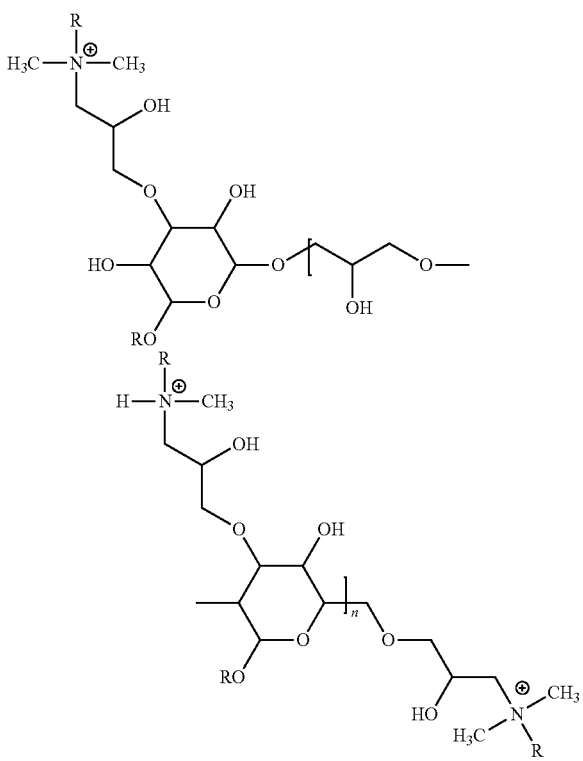

wherein R is an alkyl group having from about 6 to about 12 carbon atoms and wherein n is an integer ranging from 4 to 6,
   or a quaternized alkyl polyglucoside of the formula

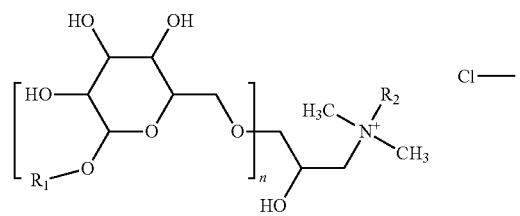

wherein $R_1$ is an alkyl group having about 6 to about 22 carbon atoms and $R_2$ is $CH_3(CH_2)_x$ where x is an integer ranging from 0 to 21 and wherein n is the degree of polymerization of 1-2;
   (c) water or other suitable diluents; and
   (d) a foam boosting surfactant in an amount up to about 18 wt. %, wherein said foam boosting surfactant is selected from the group consisting of nonionic surfactants, cationic surfactants, amphoteric surfactants, and combinations thereof, wherein the amphoteric surfactants are selected from the group consisting of imidiazolines, imidiazoline derivatives, isethionates, and combinations thereof;
   wherein the relative weight ratio of cationic active ingredient to quaternized sugar-derived surfactant to foam boosting surfactant is from about 1:0.2:0.2 to about 1:3:8;

wherein the composition provides a foam height of about 275 mL to about 350 mL;

wherein the composition does not contain anionic surfactants or lower alcohols;

wherein the composition exhibits cidal activity;

wherein the composition provides a log reduction in bacteria of at least 3 in 30 seconds or less;

wherein the composition is free of triclosan (2,4,4"-trichloro-2"-hydroxy-diphenylether); and wherein the composition has a pH range from about 7.0 to about 12.0.

2. The composition of claim 1, wherein the composition comprises about 2 wt, % to about 8 wt. % cationic active ingredients.

3. The composition of claim 1, wherein the composition comprises about 50 ppm to about 5,000 ppm cationic active ingredients.

4. The composition of claim to wherein the composition comprises about 0.5 wt. % to about 12 wt. % quaternized sugar-derived surfactant.

5. The composition of claim 1, wherein the composition comprises about 50 ppm to about 2,500 ppm quaternized sugar-derived surfactant.

6. The composition of claim 1, wherein R of the quaternized alkyl polyglucoside is an alkyl group having from about 10 to about 12 carbon atoms and wherein $R_1$ of the polyquaternized alkyl polyglucoside is an alkyl group having about 10 to about 12 carbon atoms and $R_2$ of the polyquaternized alkyl polyglucoside is $CH_3$.

7. The composition of claim 1, wherein the composition comprises up to about 9 wt. % foam boosting surfactants.

8. The composition of claim 1, wherein the composition comprises up to about 3,500 ppm foam boosting surfactants.

9. The composition of claim 1, wherein the nonionic surfactants are selected from the group consisting of alkyl amine oxide, alkyl ether amine oxide, alkyl alcohol alkoxylates, aryl alcohol alkoxylates, substituted alcohol alkoxylates, block nonionic copolymers, heteric nonionic copolymers, alkanolamides, or polyethoxylated glycerol esters.

10. The composition of claim 1, wherein the cationic surfactants are selected from the group consisting of quaternized polysaccharides, alkyl poly saccharides, alkoxylated amines, alkoxylated ether amine, phospholipids and phospholipid derivatives.

11. The composition of claim 1, wherein the composition is diluted with water or other suitable diluent to form a use solution.

12. The composition of claim 1, wherein the composition further comprises up to about 40 wt. % adjuvants.

13. The composition of claim 1, wherein the composition further comprises about 50 ppm to about 10,000 ppm adjuvants.

* * * * *

UNITED STATES PATENT AND TRADEMARK OFFICE
CERTIFICATE OF CORRECTION

PATENT NO. : 8,933,055 B2  
APPLICATION NO. : 13/238860  
DATED : January 13, 2015  
INVENTOR(S) : Daniel E. Pedersen et al.

Page 1 of 1

It is certified that error appears in the above-identified patent and that said Letters Patent is hereby corrected as shown below:

In the Claims

Col. 25, Claim 2, Line 13:
DELETE after about "2 wt, % to about 8 wt. %"
ADD after about --2 wt. % to about 18 wt. %--

Signed and Sealed this
Fifth Day of May, 2015

Michelle K. Lee
*Director of the United States Patent and Trademark Office*